US012618100B2

(12) United States Patent
Sekinger et al.

(10) Patent No.: US 12,618,100 B2
(45) Date of Patent: May 5, 2026

(54) RAPID CELLULAR LYSIS BY REDUCTION/OXIDATION REACTION

(71) Applicant: LUMINEX CORPORATION, Austin, TX (US)

(72) Inventors: Edward A. Sekinger, Austin, TX (US); Megan Martinez, Austin, TX (US); Mahima Pancholi, Austin, TX (US); Kurt Hoffacker, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 314 days.

(21) Appl. No.: 16/994,763

(22) Filed: Aug. 17, 2020

(65) Prior Publication Data

US 2021/0054444 A1      Feb. 25, 2021

Related U.S. Application Data

(60) Provisional application No. 62/889,160, filed on Aug. 20, 2019.

(51) Int. Cl.
*C12Q 1/68*          (2018.01)
*C12Q 1/6806*        (2018.01)
*C12Q 1/6844*        (2018.01)

(52) U.S. Cl.
CPC ......... *C12Q 1/6844* (2013.01); *C12Q 1/6806* (2013.01); *C12Q 2537/157* (2013.01); *C12Q 2537/159* (2013.01)

(58) Field of Classification Search
None
See application file for complete search history.

(56) References Cited

U.S. PATENT DOCUMENTS

| | | | |
|---|---|---|---|
| 2007/0292884 A1 | 12/2007 | McGill | |
| 2013/0084626 A1* | 4/2013 | Choczaj | C11D 3/38627 |
| | | | 435/264 |
| 2013/0323815 A1* | 12/2013 | Gundling | C12N 1/06 |
| | | | 435/270 |
| 2014/0010710 A1* | 1/2014 | Larson | A61L 2/16 |
| | | | 422/28 |
| 2018/0016623 A1* | 1/2018 | McFall | C12Q 1/6806 |

FOREIGN PATENT DOCUMENTS

AU        2013205379 A1 *  5/2013  ........... C12Q 1/6806

OTHER PUBLICATIONS

Goldenberger, D. et al. A simple universal DNA extraction procedure using SDS and proteinase k is compatible with direct PCR amplification. Genomme Res., vol. 4, p. 368-370, (1995).*
International Search Report and Written Opinion, issued in PCT/US2020/046608, mailed Nov. 10, 2020.
Natarajan, et al., "A Modified SDS-Based DNA Extraction Method for High Quality Environmental DNA from Seafloor Environments," Front Microbiol., 7:986, 2016.
Qamar, et al., "Optimization of conditions to extract high quality DNA for PCR analysis from whole blood using SDS-proteinase K method," *Saudi J. Biol. Sci.*, 24:1465-9, 2017.

* cited by examiner

*Primary Examiner* — Suryaprabha Chunduru
(74) *Attorney, Agent, or Firm* — pH IP Law

(57) ABSTRACT

Provided herein are methods for the rapid preparation of amplifiable nucleic acids from biological samples, which can be applied to various applications, such as, for example, point-of-care diagnostics, service laboratory diagnostics, and molecular biology applications. These methods can be performed in 15 minutes or less, and preferably in 5 minutes or less. For most applications, no further purification of nucleic acids is needed.

15 Claims, 1 Drawing Sheet

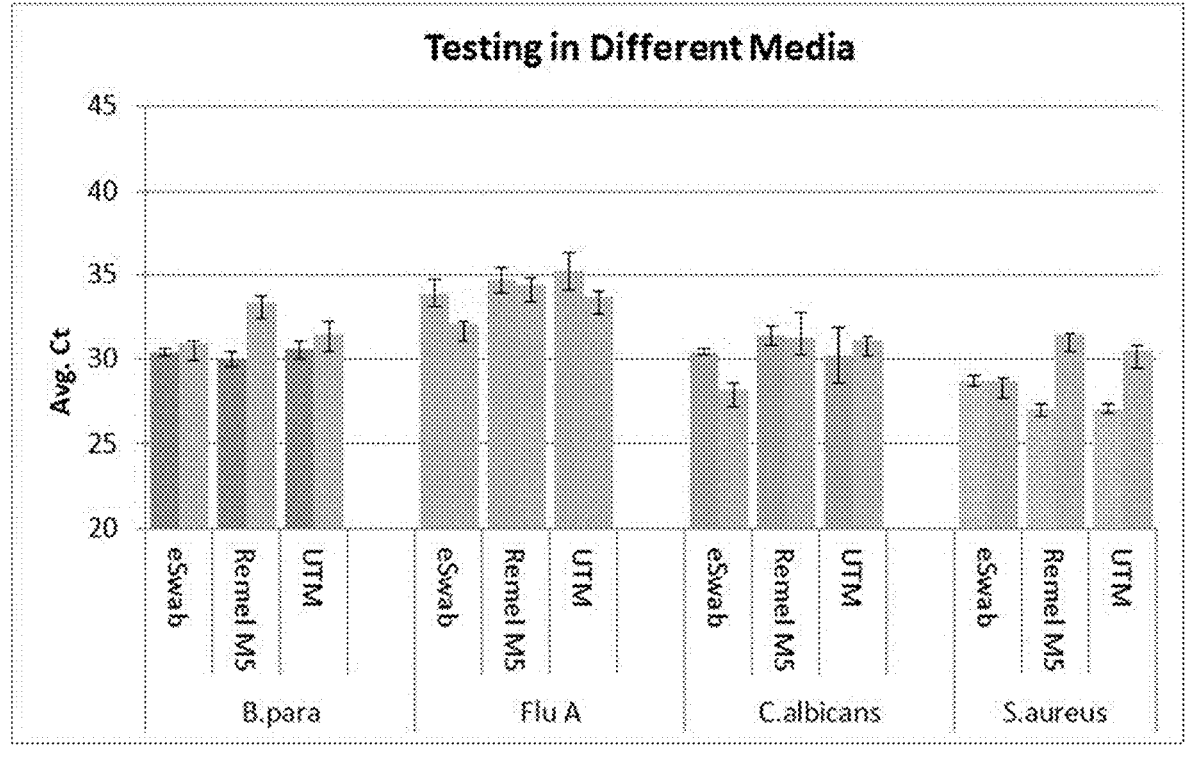

RAPID CELLULAR LYSIS BY REDUCTION/OXIDATION REACTION

CROSS-REFERENCE TO RELATED APPLICATIONS

This application claims priority to U.S. Provisional Patent Application Ser. No. 62/889,160, filed Aug. 20, 2019, the entire contents of which are incorporated herein by reference.

BACKGROUND

1. Field

The present invention relates generally to the field of molecular biology. More particularly, it concerns methods for rapid cellular lysis using a reduction-oxidation reaction in order to obtain amplifiable nucleic acids.

2. Description of Related Art

PCR and RT-PCR reactions require an input of nucleic acids that are often obtained by purifying DNA/RNA from a solid phase surface. These methods can be time consuming due to the requirements of nucleic acid binding, washing, and eluting from the surface. Methods are needed that provide amplifiable nucleic acids on a shortened time scale.

SUMMARY

As such, provided herein are methods for fast cell lysis and nucleic acid preparation. The methods may be automated or performed manually. In some aspects, these methods do not use inhibitory reagents (e.g., certain denaturants, chaotropic agents, organic solvents) that would need to be washed away before performing DNA or RNA amplification. However, a certain amount of inhibitory reagents are tolerated in the amplification reaction.

In one embodiment, provided are methods of obtaining amplifiable nucleic acids from a biological sample, the methods comprising: (a) forming a redox reaction composition by contacting the biological sample with a percarbonate salt, a nuclease suppressor, and a chelator; (b) incubating the redox reaction composition at a first temperature that is between 20° C. and 65° C.; and (c) incubating the redox reaction composition at a second temperature that is between 60° C. and 100° C.

In some aspects, the first temperature is between about 25° C. and 65° C., 35° C. and 65° C., 45° C. and 65° C., 50° C. and 65° C., 20° C. and 60° C., 25° C. and 60° C., 30° C. and 60° C., 35° C. and 60° C., 45° C. and 60° C., 20° C. and 55° C., 25° C. and 55° C., 30° C. and 55° C., 35° C. and 55° C., 40° C. and 55° C., 20° C. and 50° C., 25° C. and 50° C., 30° C. and 50° C., 35° C. and 50° C., 20° C. and 45° C., 25° C. and 45° C., 30° C. and 45° C., 20° C. and 40° C., 25° C. and 45° C., 20° C. and 35° C., or any range derivable therein. In some aspects, the first temperature is about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C.

In some aspects, step (b) comprises incubating the redox reaction composition at the first temperature for between about 1 minute and about 3 minutes, for between about 1 minute and about 2 minutes, for between about 2 minutes and about 3 minutes, for between about 90 seconds and about 3 minutes, or any range derivable therein. In some aspects, step (b) comprises incubating the redox reaction composition at the first temperature for about 60 seconds, about 75 seconds, about 90 seconds, about 105 seconds, about 120 seconds, about 135 seconds, about 150 seconds, about 165 seconds, or about 180 seconds.

In some aspects, the second temperature is between about 60° C. and 75° C., 60° C. and 80° C., 60° C. and 85° C., 60° C. and 90° C., 60° C. and 95° C., 65° C. and 80° C., 65° C. and 85° C., 65° C. and 90° C., 65° C. and 95° C., 65° C. and 100° C., 70° C. and 85° C., 70° C. and 90° C., 70° C. and 95° C., 70° C. and 100° C., 75° C. and 90° C., 75° C. and 95° C., 75° C. and 100° C., 80° C. and 95° C., 80° C. and 100° C., 85° C. and 100° C., or any range derivable therein. In some aspects, the second temperature is about 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

In some aspects, step (c) comprises incubating the redox reaction composition at the second temperature for between about 30 seconds and about 90 seconds, for between about 30 and 60 seconds, for between about 60 and 90 second, or any range derivable therein. In some aspects, step (c) comprises incubating the redox reaction composition at the second temperature for about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, or about 90 seconds.

In some aspects, the methods further comprise agitating the redox reaction composition. In some aspects, agitating comprises mechanical agitating (e.g., vortexing) or sonication.

In some aspects, the redox reaction composition is agitated during the incubation at the first temperature, between the incubation at the first temperature and the incubation at the second temperature, during the incubation at the second temperature, and/or after the incubation at the second temperature. In certain aspects, the redox reaction composition is agitated (i) between the incubation at the first temperature and the incubation at the second temperature and (ii) after the incubation at the second temperature. In one aspect, the redox reaction composition is agitated (i) for between about 15 second and 90 seconds between the incubation at the first temperature and the incubation at the second temperature and (ii) again for between about 15 seconds and 90 seconds (ii) after the incubation at the second temperature.

In certain aspects, the redox reaction composition is agitated for between about 15 and 45 seconds, for between about 15 and 60 seconds, for between about 15 and 75 seconds, for between about 15 seconds and about 90 second, for between about 30 and 60 seconds, for between about 30 and 75 seconds, for between about 30 and 90 seconds, for between about 45 and 75 seconds, for between about 45 and 90 seconds, for between about 60 and 90 seconds, or any range derivable therein. In some aspects, the redox reaction composition is agitated for about 15 seconds, 20 seconds, 25 seconds, 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, or about 90 seconds.

In some aspects, the methods further comprise contacting the biological sample with beads. In certain aspects, the beads are silica beads or glass beads. In certain aspects, the beads are metal beads.

In some aspects, the methods are performed in less than 15 minutes. In some aspects, the methods are performed in less than 5 minutes.

In some aspects, the percarbonate salt comprises sodium percarbonate. In some aspects, the nuclease suppressor comprises Proteinase K. In some aspects, the chelator comprises ethylenediaminetetraacetic acid (EDTA).

In some aspects, the biological sample may be between about 50 µL and about 300 µL, such as 50 µL, 75 µL, 100 µL, 125 µL, 150 µL, 175 µL, 200 µL, 225 µL, 250 µL, 275 µL, or 300 µL, or any other value derivable therein. In some aspects, the biological sample is diluted in a buffer prior to forming the redox reaction composition. In some aspects, the biological sample is diluted from between about 1:1 and about 1:5, from between about 1:1 and 1:4, from between about 1:1 and 1:3, from between about 1:1 and 1:2, from between about 1:2 and 1:5, from between about 1:2 and 1:4, from between about 1:2 and 1:3, from between about 1:3 and 1:5, from between about 1:3 and 1:4, from between about 1:4 and 1:5, or any range derivable therein, in a buffer prior to forming the redox reaction composition. In some aspects, the biological sample is diluted about 1:1, 1:2, 1:3, 1:4, or 1:5 in a buffer prior to forming the redox reaction composition. In certain aspects, the buffer is Tris.

In some aspects, the nucleic acids comprise DNA. In some aspects, the nucleic acids comprise RNA. In some aspects, the nucleic acids comprise a combination of DNA and RNA. In some aspects, the nucleic acids are double-stranded. In some aspects, the nucleic acids are single-stranded.

In some aspects, the biological sample comprises bacterial cells, viruses, parasitic cells, and/or eukaryotic cells. In certain aspects, the eukaryotic cells are plant cells, fungal cells, or mammalian cells. In certain aspects, the fungal cells are yeast cells, mold cells, or mushroom cells. In certain aspects, the mammalian cells are human cells, primate cells, or canine cells.

In some aspects, the amplifiable nucleic acids are suitable for use as a template in a PCR and/or RT-PCR. In some aspects, the method further comprises amplifying at least a portion of the amplifiable nucleic acids. In certain aspects, amplifying comprises performing PCR or RT-PCR.

In some aspects, no neutralization step is performed on the redox reaction composition prior to amplifying at least a portion of the amplifiable nucleic acids. In some aspects, neither sodium bicarbonate nor sodium thiosulfate are added to the redox reaction composition prior to amplifying at least a portion of the amplifiable nucleic acids. In some aspects, no wash step is performed on the redox reaction composition prior to amplifying at least a portion of the amplifiable nucleic acids.

In some aspects, the redox reaction composition is diluted in a buffer prior to amplifying at least a portion of the amplifiable nucleic acids by PCR or RT-PCR. In some aspects, the redox reaction composition is diluted from between about 1:1 and about 1:5, from between about 1:1 and 1:4, from between about 1:1 and 1:3, from between about 1:1 and 1:2, from between about 1:2 and 1:5, from between about 1:2 and 1:4, from between about 1:2 and 1:3, from between about 1:3 and 1:5, from between about 1:3 and 1:4, from between about 1:4 and 1:5, or any range derivable therein, in a buffer prior to amplifying at least a portion of the amplifiable nucleic acids by PCR or RT-PCR. In some aspects, the biological sample is diluted about 1:1, 1:2, 1:3, 1:4, or 1:5 in a buffer prior to amplifying at least a portion of the amplifiable nucleic acids by PCR or RT-PCR.

In one embodiment, provided herein are dried form compositions comprising a percarbonate salt, a nuclease suppressor, and a chelator. In some aspects, the percarbonate salt comprises sodium percarbonate. In some aspects, the nuclease suppressor comprises a proteinase, such as Proteinase K. In some aspects, the chelator comprises ethylenediaminetetraacetic acid (EDTA). In certain aspects, the composition further comprises beads, such as, for example, silica beads. In some aspects, the composition is essentially free of ascorbic acid. In some aspects, the composition is essentially free of a detergent. In some aspects, the dried composition comprises a water content that is less than about 5%, 3%, 2%, 1% or 0.5% by volume. In certain aspects, the composition is essentially free of water. In still further aspects, there is provide a sealed container comprising a dried form composition comprising a percarbonate salt, a nuclease suppressor, and a chelator of the embodiments. In yet a further aspect, there is provided a sealed multi-well plate wherein a plurality of the wells comprise a dried form composition of the embodiments.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or plus or minus 5% of the stated number.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Rapid Lysis of Samples in Various Media Using the Redox Protocol. In each pair of bars, the left bar represents the Redox Protocol and the right bar represents the ARIES benchtop.

DETAILED DESCRIPTION

Provided herein are methods for the rapid preparation of nucleic acids from biological samples, which can be applied to various point-of-care diagnostic applications. These methods can be performed in 15 minutes or less, and preferably in 5 minutes or less. For most applications, no further purification of nucleic acids is needed. As such, the methods lack reagents that are inhibitory to PCR and RT-PCR, such as, for example, strong denaturants or chaotropic agents (e.g., guanidinium isothiocyanate (GITC)) and/or organic solvents (e.g., isopropyl alcohol (IPA)). Nevertheless, a certain amount of inhibitory reagents may be present. However, the concentration of any inhibitory reagents will be too low to be significantly inhibitory to a PCR or RT-PCR reaction and thus are tolerated in the amplification reaction.

Provided here is a general description of a protocol according to one embodiment of the invention: Prior to the initial redox reaction, beads (e.g., silica low-binding beads) are added to the biological sample. In some aspects, 10-50 milligrams of silica low binding beads, such as 100 micron beads may be used. The volume of the biological sample can be varied at least depending on the amount of material available. The redox reaction comprises adding sodium percarbonate (e.g., at least about 35 mM final concentration), a chelator (e.g., at least about 0.1 mM final concentration of EDTA), and a nuclease suppressor (e.g., such as a Proteinase) to the biological sample. The sodium percarbonate generates $H_2O_2$, which damages cells, thereby making them more susceptible to lysis. The chelator (e.g., EDTA) is added to the sample to inhibit DNase. The nuclease suppressor (e.g., Proteinase K) is added to the sample to inhibit RNase. The redox reaction is incubated for about two minutes at about 60° C. The sample is then heated for about one minute at about 80° C., and then sonicated for about one minute. Finally, the lysate is diluted at least 1:4 in a pH buffered solution (e.g., a Tris buffered solution having a pH of about 6.5 to 7.5) and added directly to an amplification reaction, such as, for example, a RT-PCR reaction master mix.

By "biological sample" is meant a sample comprising any biological material which samples can be prepared for use in the method of this invention. This includes, but is not limited to, bacterial cultures, yeast cultures, cells infected with virus, isolated virus, tissue cultures, cell lines, foods contaminated with bacteria, blood, serum, patient samples, urine, and other body fluids.

By "lysis" of a cell is intended the disruption, rupture, poration, permeabilization, digestion, or break down of the cell membrane (and cell wall, where applicable) such that the nucleic acid components of the cell can be released into the external solution. According to the invention, the cell membrane need not be completely disrupted, ruptured, permeabilized or digested in order to effect the release of the nucleic acids.

By "chelator" is meant chemical compounds that react with metal ions to form a stable, water-soluble complex. The chelator is typically provided in a concentrated aqueous solution that is pH-adjusted with small amounts of concentrated acid or base, as appropriate, to achieve a pH in the physiological range. Alternatively, any of several well-known buffers can be used to adjust the pH. The chelator will have a pH of about pH 7.0 to about pH 8.0, preferably a pH of about 7.5+/−0.1 pH units. The chelator may be ethylenediaminetetraacetic acid (EDTA) or ethylene glycol-bis(2-aminoethylether) tetraacetic acid (EGTA), or their salts; more preferably, the chelating agent is EDTA. The terms "EDTA" and "EGTA" will be used to refer both to the acid and the salt form, and either form may be used in the present invention, although the salt forms are preferred.

By "nuclease suppressor" is meant an agent that inhibits the function of any nucleases present in a biological sample. Such nuclease suppressors may function by degrading any nuclease enzymes present. For example, the nuclease suppressor may be a non-specific protease, such as, for example, Proteinase K. Incubating the biological sample with Proteinase K will digest any protein present in the sample, including nucleases. The protease can be added to the sample after the chelator or simultaneously with the chelator. In order to accomplish digestion of the protein present, the biological sample with the added protease will be incubated at a temperature (e.g., between about 50° C. and about 65° C., preferably about 60° C.) and for a time (e.g., about 1 minute, about 2 minutes, about 3 minutes, about 4 minutes, or about 5 minutes) sufficient to allow the protease to work. These conditions are well known and readily determined by one of ordinary skill in the art.

As used herein "nucleic acid" means either DNA or RNA, either single-stranded or double-stranded.

As used herein, "amplification" or "amplifying" refers to the in vitro production of additional copies of a target nucleic acid sequence. Amplification is generally carried out using polymerase chain reaction (PCR) technologies known in the art. The term "amplification reaction" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 μL. "Reverse transcription PCR," or "RT-PCR," means a PCR that is preceded by a reverse transcription reaction that converts a target RNA to a complementary single stranded DNA, which is then amplified, e.g., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., U.S. Pat. No. 5,210,015 ("Taqman"); U.S. Pat. Nos. 6,174,670 and 6,569,627 (intercalating dyes); U.S. Pat. No. 5,925,517 (molecular beacons). Detection chemistries for real-time PCR are reviewed in Mackay et al., Nucleic Acids Research, 30:1292-1305 (2002). "Nested PCR" means a two-stage PCR wherein the amplicon of a first PCR becomes the sample for a second PCR using a new set of primers, at least one of which binds to an interior location of the first amplicon. "Initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture. Usually, distinct sets of primers are employed for each sequence being amplified. "Quantitative PCR" means a PCR designed to measure the abundance of one or more specific target sequences in a sample or specimen.

The amplification methods described herein may include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

The RT-PCR-grade nucleic acids can be detected and/or analyzed by any conventional detection technique, including e.g., amplification techniques such as PCR, TMA, NASBA, RT-PCR, optionally followed by sequencing analysis, if it is desirable for determination of, e.g., the types, species, and strains of microorganism detected.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Rapid Lysis Using the ≤15 Minute Redox Protocol

Multiple DNA/RNA targets were assayed using a pathogen cocktail. The pathogen cocktail was comprised of RNA viruses (Flu A and Flu B), a gram-negative bacteria (*Bordetella parapertussis*), a gram-positive bacteria (*S. aureus*), and a yeast (*C. albicans*).

Prior to the initial redox reaction, about 30 milligrams of 100 micron silica low-binding beads were added to 100 μL of the pathogen cocktail. The redox reaction comprised adding sodium percarbonate (35 mM final concentration), proteinase K (0.04 mg), and EDTA (0.1 mM final concentration) to the pathogen cocktail. The redox reaction was incubated for about two minutes at about 60° C. The sample was heated for about one minute at about 80° C., and then sonicated for about one minute. Finally, the pathogen cocktail was diluted 1:4 in 50 mM Tris (pH 7) and added directly to an RT-PCR reaction master mix.

As a process control, pathogen cocktail was subjected to identical conditions except that only water was added instead of the redox reaction components. As a positive control, the pathogen cocktail was extracted and purified using a Luminex ARIES® Benchtop system. The results are provided in Table 1.

TABLE 1

| Real-time RT-PCR results for the ≤15 Minute Redox Protocol | | | | | |
|---|---|---|---|---|---|
| Pathogen | Method | Avg Ct | StdDev Ct | Avg Tm | Positivity |
| *B. parapertussis* | ARIES Benchtop | 32.8 | 0.2 | 89.4 | 100% |
| | Redox Reaction | 29.0 | 0.2 | 90.3 | 100% |
| | Process Control | 32.8 | 0.5 | 90.5 | 100% |
| *C. albicans* | ARIES Benchtop | 35.4 | 0.8 | 80.9 | 100% |
| | Redox Reaction | 30.8 | 0.2 | 81.7 | 100% |
| | Process Control | 37.8 | 1.8 | 82.1 | 100% |
| *S. aureus* | ARIES Benchtop | 34.7 | 0.3 | 78.3 | 100% |
| | Redox Reaction | 34.5 | 0.2 | 78.9 | 100% |
| | Process Control | 34.4 | 0.9 | 78.7 | 100% |
| Flu A | ARIES Benchtop | 29.5 | 0.4 | 82.9 | 100% |
| | Redox Reaction | 29.4 | 0.3 | 83.6 | 100% |
| | Process Control | 29.3 | 0.4 | 83.6 | 100% |
| Flu B | ARIES Benchtop | 26.2 | 0.8 | 79.0 | 100% |
| | Redox Reaction | 28.3 | 0.2 | 79.6 | 100% |
| | Process Control | 32.0 | 0.5 | 79.5 | 100% |

As illustrated in Table 1, the redox reaction resulted in lower target Cts, save Flu B, which is indicative of better performance than the other two methods tested, e.g., ARIES benchtop and process control. Additionally, the standard deviations were less than 1, which demonstrates good reproducibility with the redox reaction process. Avg Ct: average Ct from 6 data points (2 biological replicates and 3 technical replicates=6 Ct values); StdDev Ct: variability determined for the 6 data points; Avg Tm: average temperature required to melt the PCR product; Positivity: percentage of successful target detection from 6 amplification reactions, e.g., 6 out of 6=100%.

Example 2—Rapid Lysis Using the 5 Minute Redox Protocol

Multiple DNA/RNA targets were assayed using a pathogen cocktail. The pathogen cocktail was comprised of an RNA virus (Flu A/B), a gram-negative bacteria (*Bordetella parapertussis*), a gram-positive bacteria (*S. aureus*), and a yeast (*C. albicans*).

Prior to the initial redox reaction, about 30 milligrams of 100 micron silica low-binding beads were added to 100 μL of the pathogen cocktail. The redox reaction comprised adding sodium percarbonate (35 mM final concentration), proteinase K (0.04 mg), and EDTA (0.1 mM final concentration) to the pathogen cocktail. The redox reaction was incubated for about two minutes at about 60° C. After the redox reaction, the sample was heated for about minute at about 80° C., and then sonicated for about 60 seconds. Finally, the pathogen cocktail was diluted 1:4 in 50 mM Tris (pH 7) and added directly to an RT-PCR reaction master mix.

As a process control, pathogen cocktail was subjected to identical conditions except that only water was added instead of the redox reaction components. As a positive

US 12,618,100 B2

9 / 10 control, the pathogen cocktail was analyzed using a Luminex ARIES® Benchtop system. The results are provided in Table 2.

TABLE 2

Real-time RT-PCR results for the 5 Minute Redox Protocol

| Pathogen | Method | Avg Ct | StdDev Ct | Avg Tm | Positivity |
|---|---|---|---|---|---|
| B. parapertussis | ARIES Benchtop | 31.6 | 0.1 | 90.0 | 100% |
| | Redox Reaction | 28.9 | 0.3 | 90.0 | 100% |
| | Process Control | 30.5 | 0.5 | 90.3 | 100% |
| C. albicans | ARIES Benchtop | 32.9 | 0.7 | 81.6 | 100% |
| | Redox Reaction | 29.9 | 0.4 | 81.7 | 100% |
| | Process Control | 36.5 | 0.9 | 81.7 | 50% |
| S. aureus | ARIES Benchtop | 33.8 | 1.0 | 78.1 | 100% |
| | Redox Reaction | 32.3 | 0.5 | 78.5 | 100% |
| | Process Control | 33.0 | 0.2 | 79.0 | 100% |
| Flu A | ARIES Benchtop | 30.3 | 0.5 | 82.9 | 100% |
| | Redox Reaction | 31.9 | 0.8 | 83.1 | 100% |
| | Process Control | 31.6 | 0.3 | 83.6 | 100% |
| Flu B | ARIES Benchtop | 29.4 | 0.5 | 79.1 | 100% |
| | Redox Reaction | 29.6 | 0.7 | 79.3 | 100% |
| | Process Control | 34.2 | 0.5 | 79.6 | 100% |
| RSV | ARIES Benchtop | 29.2 | 0.2 | 75.7 | 100% |
| | Redox Reaction | 31.2 | 0.6 | 75.8 | 100% |
| | Process Control | 38.8 | 1.3 | | 0% |

As displayed in Table 2, the redox reaction resulted in lower target Cts for DNA targets, but RNA target Cts were slightly higher than ARIES benchtop. Avg Ct: average Ct from 9 data points (3 biological replicates and 3 technical replicates=9 Ct values); StdDev Ct: variability determined for the 9 data points; Avg Tm: average temperature required to melt the PCR product; Positivity: percentage of successful target detection from 9 amplification reactions, e.g., 9 out of 9=100%.

Example 3—Rapid Lysis of Samples in Various Media Using the 5 Minute Redox Protocol The same experiment as described in Example 1 was performed, except that the pathogen cocktail also contained media. Three different types of media were tested to determine if they inhibited the 5 minute redox lysis protocol. The media tested were eSwab™ (Copan), MicroTest™ M5™ (Remel™, Thermo Fisher), and UTM™ (Copan). As a positive control, the samples were also analyzed using a Luminex ARIES® Benchtop system. The graph in FIG. 1 shows that none of the media inhibited the 15 minute redox lysis protocol, relative to the positive control.

Example 4—Rapid Lysis of Clinical Samples Using the 5 Minute Redox Protocol

The same experiment as described in Example 2 was performed, except that the samples tested were clinical samples known to be positive for the pathogens indicated in Table 3. Four different pathogens were tested: Flu A, Flu B, RSV, and C. albicans. As a positive control, the samples were analyzed using a Luminex ARIES® Benchtop system. The results are provided in Table 3.

TABLE 3

Real-time RT-PCR results for the 5 Minute Redox Protocol using Clinical Samples

| Pathogen | Method | Avg Ct | StdDev Ct | Avg Tm | Positivity |
|---|---|---|---|---|---|
| C. albicans | ARIES Benchtop | 20.7 | 0.5 | 81.6 | 100% |
| | Redox Reaction | 20.6 | 0.2 | 82.0 | 100% |
| Flu A - Sample 1 | ARIES Benchtop | 34.7 | n/a | 82.6 | 100% |
| | Redox Reaction | 36.1 | 0.4 | 83.0 | 100% |
| Flu A - Sample 2 | ARIES Benchtop | 34.1 | n/a | 83.0 | 100% |
| | Redox Reaction | 34.2 | 0.1 | 83.5 | 100% |
| Flu B - Sample 1 | ARIES Benchtop | 30.1 | n/a | 80.4 | 100% |
| | Redox Reaction | 29.7 | 0.5 | 80.5 | 100% |
| Flu B - Sample 2 | ARIES Benchtop | 30.9 | n/a | 80.8 | 100% |
| | Redox Reaction | 31.5 | 0.3 | 81.0 | 100% |
| RSV - Sample 1 | ARIES Benchtop | 26.0 | n/a | 75.9 | 100% |
| | Redox Reaction | 27.5 | 0.5 | 76.3 | 100% |
| RSV - Sample 2 | ARIES Benchtop | 30.9 | n/a | 75.6 | 100% |
| | Redox Reaction | 33.9 | 0.5 | 76.4 | 100% |

Table 3 highlights the positivity testing of clinical samples when using the redox reaction, relative to the reference method of ARIES benchtop. Avg Ct: average Ct from 3 data points (1 biological extraction and 3 technical replicates=3 Ct values); StdDev Ct: variability determined for the 3 data points; Avg Tm: average temperature required to melt the PCR product; Positivity: percentage of successful target detection from 3 amplification reactions, e.g., 3 out of 3=100%.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for preparing amplifiable nucleic acids from a biological sample, the method comprising:

(a) contacting the biological sample with a percarbonate salt, a nuclease suppressor, and a chelator to form a redox reaction composition;

(b) incubating the redox reaction composition at a first temperature, wherein the first temperature is from 20° C. to 65° C., wherein the redox composition is incubated at the first temperature for 1 to 3 minutes; and (c) incubating the redox reaction composition at a second temperature, wherein the second temperature is from 60° C. to 100° C., wherein the redox reaction composition is incubated at the second temperature for 30 to 90 seconds, thereby obtaining amplifiable nucleic acids from the biological sample without purification of the nucleic acids following the redox reaction.

2. The method of claim 1, wherein the first temperature is from 35° C. to 60° C.

3. The method of claim 1, wherein the second temperature is from 70° C. to 95° C.

4. The method of claim 1, wherein the method further comprises agitating the redox reaction mixture by mechanical agitating or sonicating.

5. The method of claim 1, further comprising contacting the biological sample with beads.

6. The method of claim 5, wherein the beads are silica beads or glass beads.

7. The method of claim 1, wherein the percarbonate salt comprises sodium percarbonate.

8. The method of claim 1, wherein the nuclease suppressor comprises Proteinase K.

9. The method of claim 1, wherein the chelator comprises ethylenediaminetetraacetic acid (EDTA).

10. The method of claim 1, wherein the method further comprises amplifying at least a portion of the amplifiable nucleic acids.

11. The method of claim 10, wherein neither sodium bicarbonate nor sodium thiosulfate are added to the redox reaction composition prior to amplifying at least a portion of the amplifiable nucleic acids.

12. The method of any of claim 10, wherein no wash step is performed on the redox reaction composition prior to amplifying at least a portion of the amplifiable nucleic acids.

13. The method of claim 1, wherein the redox reaction composition does not contain a detergent.

14. The method of claim 1, wherein the method is performed in 15 minutes or less.

15. The method of claim 1, wherein the method is performed in 5 minutes or less.

* * * * *